United States Patent
Boschat et al.

(10) Patent No.: US 6,790,994 B2
(45) Date of Patent: Sep. 14, 2004

(54) METHODS FOR HYDROGENATING NITRILE FUNCTIONS INTO AMINE FUNCTIONS

(75) Inventors: Vincent Boschat, Vichy (FR); Philippe Leconte, Meyzieu (FR)

(73) Assignee: Rhodia Polyamide Intermediates, Saint Fons (FR)

( * ) Notice: Subject to any disclaimer, the term of this patent is extended or adjusted under 35 U.S.C. 154(b) by 0 days.

(21) Appl. No.: 10/220,821

(22) PCT Filed: Mar. 7, 2001

(86) PCT No.: PCT/FR01/00687

§ 371 (c)(1),
(2), (4) Date: Jan. 10, 2003

(87) PCT Pub. No.: WO01/66511

PCT Pub. Date: Sep. 13, 2001

(65) Prior Publication Data

US 2003/0144552 A1 Jul. 31, 2003

(30) Foreign Application Priority Data

Mar. 8, 2000 (FR) .............................. 00 02997

(51) Int. Cl.⁷ .............................. C07C 209/48
(52) U.S. Cl. .................. 564/415; 564/490; 564/491; 564/492; 564/493
(58) Field of Search ...................... 564/415, 490–493

(56) References Cited

FOREIGN PATENT DOCUMENTS

| | | |
|---|---|---|
| DE | 22 38 452 | 2/1974 |
| EP | 0 303 550 | 2/1989 |
| FR | 2 068 953 | 9/1971 |
| FR | 2 773 086 | 7/1999 |
| WO | WO 95/17959 | 7/1995 |
| WO | WO 95/18090 | 7/1995 |
| WO | WO 97/10052 | 3/1997 |
| WO | WO 98/43941 | 10/1998 |

OTHER PUBLICATIONS

Database CAPLUS on STN, Acc. No. 1967:406057, Orito et al., Tokyo Kogyo Shikensho Hokoku (1967), 62(1), p. 34–7 (abstract).*

* cited by examiner

Primary Examiner—Brian J. Davis
(74) Attorney, Agent, or Firm—Burns, Doane, Swecker & Mathis, L.L.P.

(57) ABSTRACT

The present invention relates to a process for the hydrogenation of nitrile functional groups to amine functional groups. It relates more particularly to a process for the complete or partial hydrogenation of dinitrile compounds to diamine or aminonitrile compounds.

The invention relates to a process for the hydrogenation of nitrile functional groups to amine functional groups using hydrogen in the presence of a hydrogenation catalyst and of a strong inorganic base preferably deriving from an alkali metal or alkaline earth metal. According to the invention, the process comprises a stage of conditioning the catalyst which consists in mixing the hydrogenation catalyst, a predetermined amount of strong inorganic base and a solvent in which the strong inorganic base is not very soluble. This solvent is an amine compound, such as hexamethylenediamine in the case of the hydrogenation of adiponitrile to HMD and/or aminocapronitrile.

20 Claims, No Drawings

METHODS FOR HYDROGENATING NITRILE FUNCTIONS INTO AMINE FUNCTIONS

This application is a 371 of PCT/FR01/00687 filed Mar. 7, 2001

The present invention relates to a process for the hydrogenation of nitrile functional groups to amine functional groups.

It relates more particularly to a process for the complete or partial hydrogenation of dinitrile compounds to diamine or aminonitrile compounds.

Hydrogenation of dinitriles to the corresponding diamines is a process which has been used for a long time, in particular hydrogenation of adiponitrile to hexamethylenediamine, one of the base materials in the preparation of polyamide-6,6.

An increasing interest has become apparent in recent years in the hydrogenation (also sometimes known as hemihydrogenation) of aliphatic dinitriles to aminonitriles, in particular the hydrogenation of adiponitrile to 6-aminocapronitrile, resulting either directly or via caprolactam in polyamide-6.

Thus, U.S. Pat. No. 5,151,543 discloses a process for the selective hydrogenation of aliphatic dinitriles to the corresponding aminonitriles, at 25–150° C. and under a pressure of greater than atmospheric pressure, in the presence of a solvent in a molar excess of at least 2/1 with respect to the dinitrile, the solvent comprising liquid ammonia or an alcohol with 1 to 4 carbon atoms and an inorganic base which is soluble in the said alcohol, in the presence of a Raney catalyst, the aminonitrile obtained being recovered as main product.

Patent WO-A-93/16034 discloses a process for the preparation of 6-aminocapronitrile by hydrogenation of adiponitrile in the presence of an inorganic base, of a transition metal complex, the transition metal being of low valency and chosen from chromium, tungsten, cobalt and iron, and of Raney nickel as catalyst, under hydrogen pressure and at a temperature of 50° C. to 90° C.

Patent WO-A-96/18603 discloses the hemihydrogenation of aliphatic dinitriles to aminonitriles by hydrogen in the presence of a catalyst based on optionally doped Raney cobalt or nickel and of a strong inorganic base, the starting hydrogenation medium comprising water, aminonitrile and/or diamine which are capable of being formed and unconverted dinitrile.

All these hydrogenation processes result in the desired aminonitrile and are presented as being able to be employed continuously in an industrial plant.

However, the selectivities and the yields of these processes have to be improved to render them more competitive.

One of the aims of the present invention is to provide a process for the hydrogenation of nitrile functional groups in the presence of a catalyst exhibiting an improved yield and an improved selectivity.

To this end, the invention provides a process for the hydrogenation of nitrile functional groups to amine functional groups using hydrogen in the presence of a hydrogenation catalyst and of a strong inorganic base preferably deriving from an alkali metal or alkaline earth metal.

According to the invention, the process comprises a stage of conditioning the catalyst which consists in mixing the hydrogenation catalyst, a predetermined amount of strong inorganic base and a solvent in which the strong inorganic base is not very soluble. According to the invention, the medium comprising a catalyst thus conditioned is fed into the hydrogenation reactor, the hydrogenation reaction being carried out according to the usual conditions or procedures already disclosed in the literature.

The term "hydrogenation catalyst" is understood to mean, in particular and advantageously, Raney metals, such as Raney nickel or Raney cobalt, mixed oxides with a hydrotalcite structure, as disclosed in WO97/10052, but also supported metals, in particular metals from Group VIII of the Periodic Table of the Elements, such as nickel, cobalt, ruthenium or rhodium, deposited on a support, which is generally a metal oxide or active charcoal.

In the case of Raney metals, their instability on contact with the air requires the use of a liquid storage medium. This liquid medium is generally water.

According to the invention, the solvent used exhibits a good affinity for the storage liquid, generally water, thus making it possible to obtain phase separation and formation of a phase comprising the strong inorganic base at a high concentration.

According to a preferred embodiment, the strong inorganic base is added to the said storage medium before the addition of the solvent.

In the case of the other catalysts, which do not require the presence of a storage liquid, it may be worthwhile and advantageous to add water to the mixture.

The term "affinity between the solvent and the storage liquid or water" should be understood as meaning that these compounds are soluble in one another.

Likewise, the term "not very soluble" used to characterize the solubility of the strong inorganic base in the solvent should be interpreted as meaning a solubility of less than 3% by weight of the said base in the pure solvent.

According to the invention, the order of addition of the components or the mixture is immaterial.

According to the process of the invention, the presence of the solvent results in a phase separation of the strong inorganic base or of a concentrated solution of strong inorganic base, forming a second liquid phase comprising all or essentially all of the amount of base added to the mixture, this said phase comprising the strong base being and remaining in intimate contact with the catalyst, the first phase being formed by the solvent and the storage liquid and optionally the solvent of the base, if the latter is added in the form of a solution in a solvent, such as water.

Therefore, the catalyst particles come into contact with a concentrated solution of strong inorganic base, allowing the catalyst to be conditioned by attachment or adsorption of the molecules of strong base at the surface of the said catalyst.

The use of a catalyst comprising molecules of strong base at its surface makes it possible to carry out a hydrogenation with an improved yield and selectivity which are reflected in particular by a decrease in the impurities formed, as is illustrated in the examples given below.

The hydrogenation catalyst can advantageously comprise, in addition to the catalytic metal, a doping element chosen from the elements from Groups Ib, IIb, IVb, VIb, VIIb and VIII of the Periodic Table of the Elements, as published in the Handbook of Chemistry and Physics (Weast, 5th edition of 1970–1971), and aluminium, present in particular in Raney metals.

The term "Raney metal" is understood as meaning in particular Raney nickel or Raney cobalt.

The strong inorganic bases which are suitable for the invention are alkali metal or alkaline earth metal hydroxides, for example LiOH, NaOH, KOH, RbOH, CsOH, and their mixtures.

According to another characteristic of the invention, the liquid storage medium for the Raney metal is preferably water.

According to one characteristic of the invention, the amount of strong base added in the stage of conditioning the catalyst is between 0.1 mol and 50 mol per kg of catalyst. The ultimate amount of base is determined for each catalyst.

According to a preferred form of the invention, the strong base is added in the conditioning stage in the form of a concentrated solution or in the pure form.

Furthermore, the amount of solvent added depends on the degree of solubility of water or of the storage liquid in this solvent and on the desired level of concentration in the phase comprising the strong base. Advantageously, the ratio by weight of the solvent to the water (or storage liquid) will be at least equal to 1, preferably greater than or equal to 2.

According to the invention, the solvent is chosen from the compounds which have an affinity (solubilizing ability, for example) for water or the storage liquid for the Raney metal and which, in contrast, do not have an affinity (low solubilizing ability) for the strong inorganic base. The concept of insolubility of the strong base in the solvent or more specifically in the liquid phase formed by the solvent and the water or the storage liquid should be understood as meaning a low solubility of the base, for example of less than 1% by weight.

In a preferred embodiment of the invention, the solvent is advantageously an amine, preferably an amine corresponding to that obtained by the hydrogenation reaction, or liquid ammonia, in the case where the hydrogenation is carried out in a liquid ammonia medium. This is because the choice of the solvent should advantageously not allow new substances to be introduced into the hydrogenation medium and thus should make possible easy and inexpensive separation and optionally recycling processes which are thus not very penalizing for the process from a technical and economical viewpoint.

The stage of conditioning the catalyst can be carried out under an inert atmosphere, optionally under a hydrogen atmosphere or under hydrogen pressure.

The process of the invention applies more particularly to the hydrogenation of dinitriles, such as adiponitrile, to diamines, such as hexamethylenediamine (HMD), or to the partial hydrogenation or hemihydrogenation of dinitriles, such as adiponitrile, to aminonitriles, such as aminocapronitrile. The latter reaction is particularly advantageous for the manufacture of lactams, such as ε-caprolactam, obtained by cyclizing hydrolysis of the aminonitrile.

Generally, this hemihydrogenation reaction is carried out in the presence of water, which represents between 0.1 and 20% by weight of the reaction medium, or in the presence of another compound, for example liquid ammonia, the concentration of this compound advantageously being less than 50% by weight of the reaction medium.

Thus, in a specific embodiment of a hemihydrogenation, the starting hydrogenation medium comprises water in a proportion of at least 0.5% by weight with respect to all the liquid compounds of the reaction medium. The medium also comprises one or more diamines and/or aminonitriles, capable of being formed from the dinitrile by hydrogenation with hydrogen, and unconverted dinitrile in a proportion, for the combination of these three compounds, of 80% and 99.5% by weight with respect to the combined liquid compounds of the reaction medium.

The aliphatic dinitriles which can be employed in the process of the invention are more particularly the dinitriles of general formula (I):

$$NC-R-CN \qquad (I)$$

in which R represents a linear or branched alkylene or alkenylene group having from 1 to 12 carbon atoms.

Use is preferably made, in the process of the invention, of dinitriles of formula (I) in which R represents a linear or branched alkylene radical having from 2 to 6 carbon atoms.

Mention may in particular be made, as examples of such dinitriles, of adiponitrile, methylglutaronitrile, ethylsuccinonitrile, malononitrile, succinonitrile, glutaronitrile and their mixtures, in particular the mixtures of adiponitrile and/or of methylglutaronitrile and/or of ethylsuccinonitrile which can originate from the same process for the synthesis of adiponitrile.

In practice, the case where $R=(CH_2)_4$ will be the most frequent as this corresponds to the use of adiponitrile (ADN) in the present process.

It is also possible, in the process of the invention, to add a strong base to the hydrogenation reaction medium which is identical to or different from that used for the conditioning of the catalyst. This strong base is generally an alkali metal or alkaline earth metal hydroxide, carbonate or alkoxide.

The reaction medium has a composition varying according to the type of implementation of the process.

This is because, if the process is carried out batchwise, as is in particular the case in tests on the laboratory scale or for small-scale manufacturing trials, the starting reaction medium will gradually grow richer in aminonitrile and, to a lesser extent, in diamine, whereas the concentration of dinitrile can either decrease, if all or most of the said dinitrile is charged from the beginning of the hemihydrogenation, or can remain relatively constant, if the dinitrile is introduced gradually during the reaction.

In contrast, if the process is carried out continuously, the average composition of the reaction medium reaches values predetermined by the degree of conversion and the selectivities of the reaction.

Water is usually present in an amount of less than or equal to 20%. The water content of the reaction medium is preferably between 0.5% and 15% by weight with respect to the combined liquid constituents of the said medium.

The concentration of the targeted aminonitrile and/or of the corresponding diamine and of the unconverted dinitrile in the reaction medium is generally between 85% and 98% by weight with respect to the combined liquids included in the said reaction medium.

The catalysts used in this hemihydrogenation process can be a Raney nickel or a Raney cobalt comprising, in addition to the nickel or the cobalt and the residual amounts of the metal removed from the starting alloy during the preparation of the catalyst, that is to say generally aluminium, one or more other elements, often known as doping elements, such as, for example, chromium, titanium, molybdenum, copper, tungsten, iron or zinc. Among these doping elements, chromium, copper, titanium, iron and their mixtures are regarded as the most advantageous. These doping elements usually represent, by weight with respect to the weight of nickel or of cobalt, from 0% to 15% and preferably from 0% to 10%.

Use may also advantageously be made of a catalyst based on ruthenium deposited on a support composed of acetylene black. This catalyst can also comprise doping metal elements included in the list mentioned for the Raney metals.

The amount of catalyst employed can vary very widely according in particular to the nature of the catalyst and the method of operation adopted or the reaction conditions chosen. By way of indication, use may be made of 0.5% to 50% by weight of catalyst, expressed as weight of metal with respect to the total weight of the reaction medium, and generally of 1% to 35% by weight.

The process of the invention is generally carried out at a reaction temperature of less than or equal to 150° C., preferably of less than or equal to 120° C. and more preferably still of less than or equal to 100° C.

In concrete terms, this temperature is between ambient temperature (approximately 20° C.) and 100° C.

Prior to, simultaneously with or subsequent to the heating, the reaction chamber is brought to the appropriate hydrogen pressure, that is to say, in practice, between 1 bar (0.10 MPa) and 100 bar (10 MPa) and preferably between 5 bar (0.5 MPa) and 50 bar (5 MPa).

The other conditions which govern the hydrogenation (continuous or batchwise) in accordance with the invention relate to conventional technical arrangements which are known per se.

Furthermore, these conditions can be modified in order to modify the degree of conversion of the dinitrile to diamine according to whether a high selectivity for aminonitrile is desired or conversely complete hydrogenation of the dinitriles to diamines is desired.

The following examples, given solely by way of indication, illustrate the invention.

In these examples, the following abbreviations may be used:

ADN=adiponitrile
ACN=aminocapronitrile
HMD=hexamethylenediamine
DC=degree of conversion (% by weight of adiponitrile converted)
YD=selectivity with respect to the converted starting substrate (mol % of compound ACN ($YD_{ACN}$) or HMD ($YD_{HMD}$) obtained with respect to the total amount of ADN converted).

EXAMPLE 1

0.806 g of potassium hydroxide, in solution in 4.2 g of water, is mixed with 37.8 g of hexamethylenediamine in a stirred reactor.

The mixture is kept stirred at 80° C. A two-phase system is formed. The organic phase, comprising the HMD, is analysed to determine the water content and potassium hydroxide content. The results are as follows:

Water content: 8.2% by weight
Potassium hydroxide concentration: 0.0287% by weight The aqueous phase is thus an approximately 50% by weight potassium hydroxide solution.

The amount of potassium hydroxide present in the organic phase represents 1.5% of the amount of potassium hydroxide charged.

EXAMPLES 2 AND 3

Example 1 is repeated by mixing 252 g of HMD, 126 g of ethanol and 5.76 g of sodium hydroxide in solution in 42 g of water.

Analysis of the organic phase obtained after stirring shows that it comprises 7.16% by weight of water and 0.3252% of sodium hydroxide.

This result shows that approximately 25% of the sodium hydroxide charged is found in the organic phase, which comprises a solvent of the sodium hydroxide, namely ethanol.

Similar tests, without ethanol but using 378 g of HMD instead of 252 g, makes it possible to obtain a concentration of sodium hydroxide in the organic phase of 0.0496%. In this example, 3.6% of the sodium hydroxide charged is found in the organic phase.

EXAMPLE 4

Analogously to Example 1, 20 g of Raney nickel, present in 18 g of water, are mixed with 180.9 g of hexamethylenediamine and 0.896 g of potassium hydroxide in solution in 4.23 g of water. The mixture is stirred at 80° C.

Analysis of the HMD-based organic phase shows that it comprises 10.2% by weight of water and 0.0123% by weight of potassium hydroxide. The amount of potassium hydroxide present in the organic phase represents 2.8% of the potassium hydroxide charged. 97.2% by weight of the potassium hydroxide charged is thus in direct contact with the catalyst.

EXAMPLE 5

240 g of HMD, 52 g of water and 6.4 g of Raney nickel doped with 1.5% by weight of chromium are charged to a stirred reactor. 0.462 ml of a 388 g/l potassium hydroxide solution are added in order to obtain a KOH/Ni ratio of 0.5 mol/kg. The mixture is kept stirred at a temperature of 50° C. The reactor is placed under hydrogen pressure at 25 bar.

40 g of adiponitrile are added to the reactor. After reacting for 50 minutes, the medium is cooled and analysed by gas chromatography to determine the total degree of conversion (DC) of the adiponitrile (ADN), the selectivity ($YD_{ACN}$) of the reaction for aminocapronitrile (ACN) and the Poln concentration of the medium.

This polarographic number represents in particular the concentration of imine compounds in the medium. It is determined by polarography and is expressed in moles of imine functional group per tonne of sample to be quantitatively determined.

Degree of conversion of ADN (DC): 83.8%
Selectivity for ACN (YDACN): 68.3%
Poln in mol/t: 21

COMPARATIVE EXAMPLE 6

Example 5 was repeated but with addition of the potassium hydroxide simultaneously with the adiponitrile. The amounts added are identical.

The results obtained are as follows:
Degree of conversion of ADN (DC): 81.1%
Selectivity for ACN ($YD_{ACN}$): 69.7%
Poln in mol/t: 76

This results clearly shows the effect of the stage of conditioning the catalyst on the purity of the product obtained.

EXAMPLE 7 AND COMPARATIVE EXAMPLE 8

A catalyst based on ruthenium doped with 1% by weight of iron on an acetylene black support, sold under the name Y 70, is obtained by the following process:

20 g of Y70 acetylene black, sold by SN2A, are charged to 800 ml of water. The suspension is heated to 90° C. with stirring. 1.8 g of $Na_2CO_3$ in a total of 70 ml of water are added. After a period of 1 hour, a solution of 2.16 g of $RuCl_3$ hydrate in 120 ml of water is added. After 1 hour, a solution of 1 g of $FeCl_3$ hexahydrate in a total of 70 ml of water is run in. After a further hour, the medium is allowed to cool to a temperature of 40° C.

After filtration, the catalyst is washed with 4 times 200 ml of water at 40° C.

The catalyst is dried in an oven for 1 hour at 120° C. 21.3 g of catalyst are obtained.

Before the test, it is dried in an oven for 10 hours at 80° C. under reduced pressure. 2.4 g of catalyst prepared according to the above process, 4.8 g of water and 5 g of 15N potassium hydroxide are added to 36 g of HMD.

The medium is mixed at a temperature of 80° C. and placed under a hydrogen pressure of 2.5 MPa. 36 g of adiponitrile are added to this medium.

After reaction, the medium is analysed.

The following results are obtained:

reaction time: 105 min

DC of the ADN: 67%

$YD_{ACN}$ 75%

Poln 35 mol/t

A test using the procedure of Comparative Example 6 and the masses and products used in the above Example 7, in particular the same catalyst, gave the following results:

reaction time: 110 min

DC of the ADN: 68.5%

$YD_{ACN}$ 73%

Poln 92 mol/t

What is claimed is:

1. Process for the hydrogenation of nitrile functional groups to amine functional groups using hydrogen in the presence of a hydrogenation catalyst and a strong inorganic base derived from an alkali metal or alkaline earth metal, comprising conditioning the catalyst by mixing the catalyst, a predetermined amount of strong inorganic base which is associated with the catalyst and a solvent in which the strong inorganic base is not very soluble, said mixture comprising the conditioned catalyst being fed into the hydrogenation reaction medium comprising the compound to be hydrogenated and optionally a solvent.

2. Process according to claim 1, wherein the hydrogenation catalyst is selected from the group consisting of Raney metals, metals from Group VIII of the Periodic Table of the Elements deposited on a support, and mixed oxides with a hydrotalcite structure.

3. Process according to claim 2, wherein the Raney metal is Raney nickel or Raney cobalt.

4. Process according to claim 2, wherein the metals from Group VIII are selected from the group consisting of nickel, cobalt, ruthenium and rhodium, and the support being selected from the group consisting of metal oxides, active charcoal or acetylene blacks.

5. Process according to claim 1, wherein, when a liquid known as a storage liquid is associated with the use of the catalyst, said solvent and said storage liquid are soluble in one another, the strong inorganic base not being very soluble in the solution of the solvent and the storage liquid.

6. Process according to claim 1 wherein the mixture for conditioning the catalyst comprises water.

7. Process according to claim 5, wherein water is a liquid for storage of the hydrogenation catalyst.

8. Process according to claim 1, wherein the solvent is a compound comprising one or more amine functional groups or liquid ammonia.

9. Process according to claim 8, wherein the solvent is an amine compound formed by the hydrogenation reaction or is identical to a compound formed by the hydrogenation reaction.

10. Process according to claim 1, wherein the strong inorganic base is added to the liquid medium for storage of the Raney metal before the addition of the solvent.

11. Process according to claim 1, wherein the stage of conditioning the catalyst is carried out under an inert atmosphere.

12. Process according to claim 1, wherein the stage of conditioning the catalyst is carried out under a hydrogen atmosphere or hydrogen pressure.

13. Process according to claim 1, which comprises hydrogenating a dinitrile to an aminonitrile and/or to a diamine.

14. Process according to claim 13, wherein the dinitrile is adiponitrile and it comprises hydrogenating adiponitrile to aminocarpronitrile and/or hexamethylenediamine.

15. Process according to claim 13, wherein the solvent is hexamethylenediamine.

16. Process according to claim 1, wherein the ratio by mass of the solvent to the liquid medium for storage of the catalyst or the water in the mixture for conditioning the catalyst is at least equal to 1.

17. Process according to claim 1, wherein the concentration of catalyst in the conditioning mixture is less than or equal to 30% by weight, expressed as weight of metal.

18. Process according to claim 1, wherein the catalyst comprises doping elements.

19. Process according to claim 18, wherein the Raney metal is Raney nickel, the doping element or elements are selected from the group consisting of the elements from Groups Ib, IIb, IVb, VIIb and VIII of the Periodic Table of the Elements.

20. Process according to claim 18, wherein the Raney metal is Raney cobalt, the doping element or elements is selected from the group consisting of the elements from Groups Ib, IIb, IVb, VIb, VIIb and VIII of the Periodic Table of the Elements.

* * * * *